US010786259B2

(12) United States Patent
Lorenzo et al.

(10) Patent No.: US 10,786,259 B2
(45) Date of Patent: Sep. 29, 2020

(54) SPLIT BALLOON ASSIST DEVICE AND METHOD FOR USING THE SAME

(71) Applicant: DePuy Synthes Products, Inc., Raynham, MA (US)

(72) Inventors: Juan Lorenzo, Raynham, MA (US); Robert Slazas, Raynham, MA (US)

(73) Assignee: DePuy Synthes Products, Inc., Raynham ( * ) Notice: Subject to any disclaimer, the term of this patent is extended or adjusted under 35 U.S.C. 154(b) by 117 days.

(21) Appl. No.: 15/941,105

(22) Filed: Mar. 30, 2018

(65) Prior Publication Data
US 2019/0298383 A1 Oct. 3, 2019

(51) Int. Cl.
*A61B 17/12* (2006.01)
*A61M 25/10* (2013.01)
(Continued)

(52) U.S. Cl.
CPC .... *A61B 17/12136* (2013.01); *A61B 17/1204* (2013.01); *A61B 17/12109* (2013.01); *A61M 25/10* (2013.01); *A61M 25/1002* (2013.01); *A61M 25/1011* (2013.01); *A61M 25/10181* (2013.11); *A61B 17/0218* (2013.01); *A61B 2017/00557* (2013.01); *A61M 2025/1043* (2013.01); *A61M 2025/1052* (2013.01);
(Continued)

(58) Field of Classification Search
CPC ...... A61M 2025/0034; A61M 25/0068; A61M 25/1006; A61M 29/00; A61M 25/0029; A61M 2025/0183; A61M 2025/107; A61M 25/1002

USPC .......................................................... 606/194
See application file for complete search history.

(56) References Cited

U.S. PATENT DOCUMENTS 5,211,654 A    5/1993  Kaltenbach
5,549,555 A *  8/1996  Sohn ................ A61M 25/1002
                                                  604/101.01
(Continued)

FOREIGN PATENT DOCUMENTS

EP    2589344 A1    5/2013
WO    99/27989 A1   6/1999
WO    2015/061801 A2 4/2015

OTHER PUBLICATIONS

Extended European Search Report from corresponding European application No. 19166296.4, dated Aug. 29, 2019.

*Primary Examiner* — Gregory A Anderson
*Assistant Examiner* — Alyssa M Keane
(74) *Attorney, Agent, or Firm* — Troutman Pepper Hamilton Sanders LLP

(57) ABSTRACT

A balloon assist device is disclosed which includes an inner body and a balloon bonded to the inner body. The inner body extends along an axis from a proximal end to a distal end and the cross-section of the inner body partially encloses the axis. The balloon assist device also includes an inflation tube in sealed communication with the volume enclosed by the inner body and the sheath. The balloon assist device may also include a pusher for sliding the balloon assist device along the catheter. The pusher may extend parallel to the axis from the proximal end of the balloon assist device in a proximal direction. The inflation tube may also be used as a pusher. The inner body of the balloon assist device may be a split cylinder extending along the axis from the proximal end to the distal end.

12 Claims, 7 Drawing Sheets

(51) Int. Cl.
 *A61B 17/00* (2006.01)
 *A61B 17/02* (2006.01)
(52) U.S. Cl.
 CPC .............. *A61M 2025/1072* (2013.01); *A61M 2205/0216* (2013.01)

(56) References Cited

U.S. PATENT DOCUMENTS

| | | | |
|---|---|---|---|
| 5,882,334 A * | 3/1999 | Sepetka | A61M 25/01 604/164.08 |
| 6,666,828 B2 | 12/2003 | Greco et al. | |
| 7,214,198 B2 | 5/2007 | Greco et al. | |
| 2004/0176790 A1 * | 9/2004 | Coyle | A61M 25/0023 606/194 |
| 2006/0030924 A1 * | 2/2006 | Van Der Leest | A61F 2/856 623/1.11 |
| 2007/0185444 A1 * | 8/2007 | Euteneuer | A61M 25/1027 604/96.01 |
| 2011/0137331 A1 | 6/2011 | Walsh | |

* cited by examiner

SPLIT BALLOON ASSIST DEVICE AND METHOD FOR USING THE SAME

FIELD

This disclosure relates generally to the field of tools for vascular surgery. More particularly, it relates to balloon devices for occluding blood vessels during vascular surgery.

BACKGROUND

Balloon Guide Catheters facilitate the insertion of intravascular devices as well as control/restrict flow in ischemic applications. They are designed to have a large lumen to maximize clot capture, and are indicated for use as a conduit for clot retrieval devices. Because the balloon is an integral part of the assembly on these devices, the profile of the devices is very large, for example 8 F (2.7 mm) (French "F"=0.33 mm) as compared to a regular large ID guide catheter which might be sized 6 F (2.0 mm). Also, the overall flexibility of the system is decreased due to the required inflation lumen and dual layer construction needed to inflate the distal balloon. The combination of the large overall profile and the lack of distal flexibility makes tracking these devices in the neurovascular anatomy difficult. Accordingly, use of these devices is mostly limited to the proximal cerebral vasculature.

SUMMARY

To address these deficiencies in the existing art, a balloon assist device is disclosed which includes an inner body and a sheath joined to the inner body, enclosing a volume between the inner body and the sheath. The inner body extends along an axis from a proximal end to a distal end and the cross-section of the inner body partially encloses the axis. The balloon assist device also includes an inflation tube in sealed communication with the volume enclosed by the inner body and the sheath. The balloon assist device may also include a pusher for sliding the balloon assist device along the catheter. The pusher may extend parallel to the axis from the proximal end of the balloon assist device in a proximal direction. The inflation tube may also be used as a pusher. The inner body of the balloon assist device may be a split cylinder extending along the axis from the proximal end to the distal end. The inner body may be formed of a resilient material.

The split cylinder of the inner body is divided by a slit. The slit may be straight, parallel to the axis from the proximal end to the distal end or helical, extending helically about the axis from the proximal end to the distal end. The sheath may be bonded to inner body along a perimeter having four sides which follow the contours of an outer face of the split cylinder. The sheath may be an elastic material or an inelastic material.

The balloon assist device may be designed for the inner body to snap over the exterior of a catheter with the inflatable sheath bonded to the inner body, for example by passing the catheter through a slit in the inner body. The inner body may be slidable along the catheter when snapped over the exterior of the catheter. The balloon assist device may be slid along the catheter via the pusher extending from the balloon assist device in a proximal direction. The balloon assist device may include an inflation tube in sealed communication with the inflatable sheath. The inflation tube may also be used to slide the balloon assist device along the catheter. The inner body may be formed of a resilient material configured to snap over the exterior of the catheter by expanding a slit in the inner body, passing the catheter through the slit, and allowing the slit to contract around the catheter.

A balloon assisted catheter system includes a catheter and a balloon assist device including an inner body and an inflatable sheath bonded to the inner body. The inner body may include a split cylinder with a proximal and a distal end. The split cylinder may be split by a straight opening extending from the proximal end to the distal end or by a helical opening extending helically about the axis from the proximal end to the distal end. The balloon assist device may include a pusher extending from the balloon assist device in a proximal direction. The pusher may be used to slide the balloon assist device along the catheter. The balloon assist device may also include an inflation tube in sealed communication with the inflatable sheath.

A method of using a balloon assist device including the steps of expanding a slit in a resilient inner body of the balloon assist device, inserting a catheter through the expanded slit, and releasing the expanded slit to contract around the catheter. The method may also include using a pusher to slide the balloon assist device along the catheter to a treatment site in a patient's vasculature. The method may also include using an inflation tube to inflate the balloon assist device at the treatment site. The method may also include performing a surgical procedure while the inflated balloon assist device occludes a blood vessel at the treatment site. The method may also include deflating the balloon assist device and withdrawing the deflated balloon assist device.

DETAILED DESCRIPTION

Figure 1:
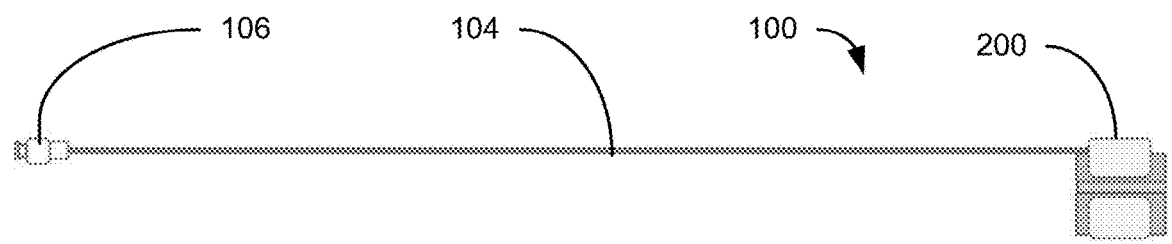
FIG. 1 is a diagram of a balloon assist device illustrating is basic components, in accordance with the present disclosure.
Figure 2:
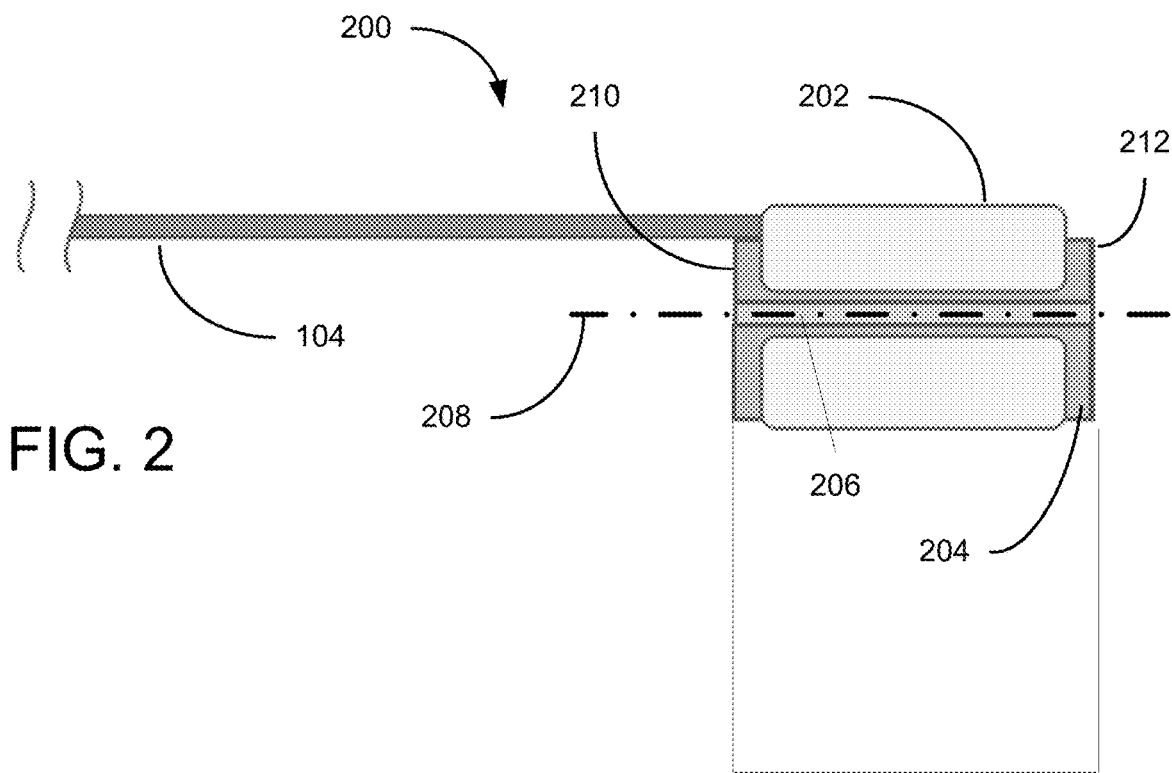
FIG. 2 is a diagram of the balloon assembly of the balloon assist device illustrating is construction, in accordance with the present disclosure.
Figure 3:
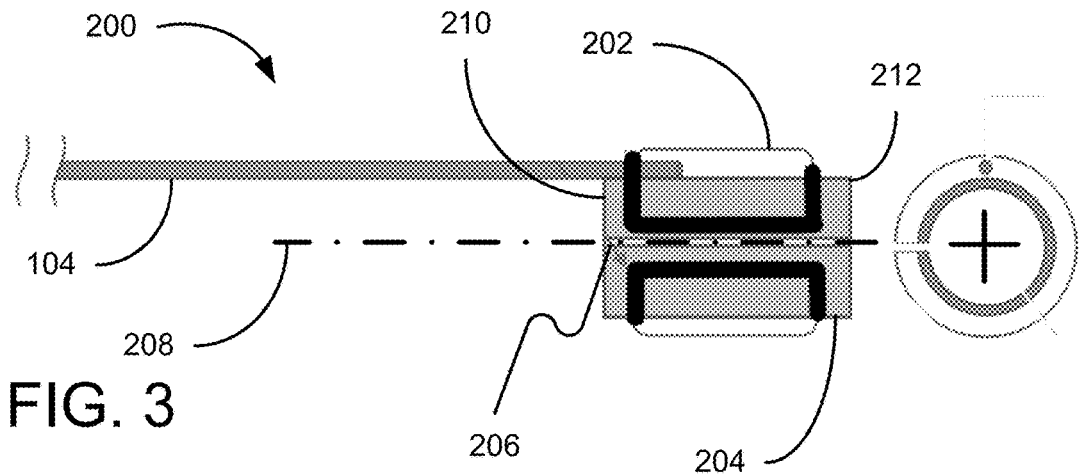
FIG. 3 is a diagram of the balloon assembly of the balloon assist device illustrating the balloon in the deflated state and highlighting the seals between the balloon and the inner body, in accordance with the present disclosure.
Figure 4:
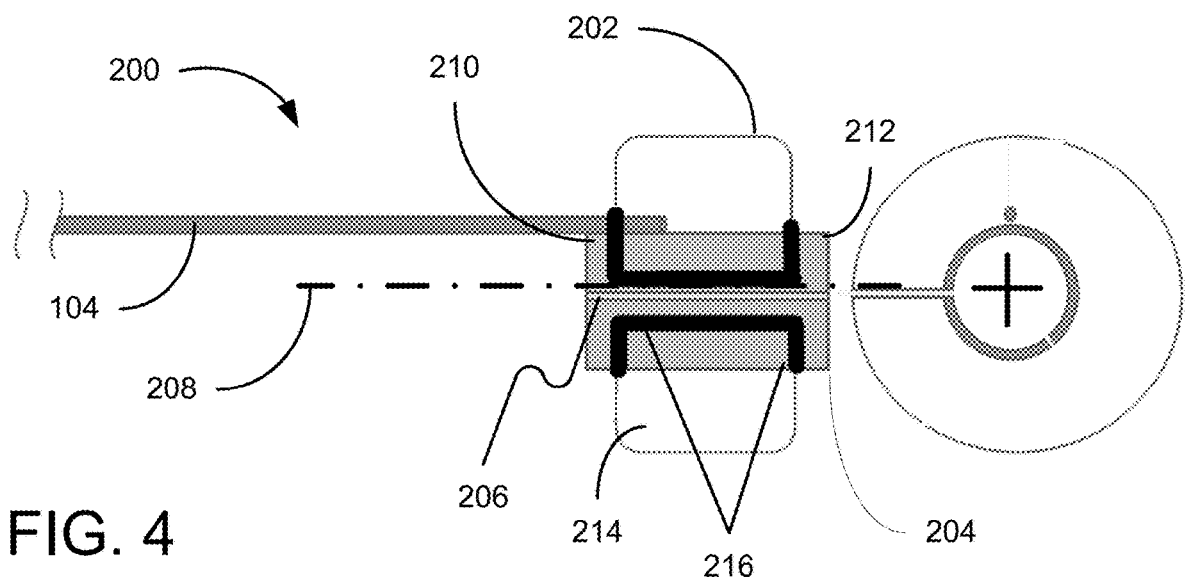
FIG. 4 is a diagram of the balloon assembly of the balloon assist device illustrating the balloon in the inflated state and highlighting the seals between the balloon and the inner body, in accordance with the present disclosure.

Referring now to the Figures, in which like reference numerals represent like parts, various embodiments of the balloon assist device and methods of using it will be disclosed in detail. FIG. 1 is a diagram of the balloon assist device 100 illustrating is basic components. The balloon assist device 100 includes a balloon assembly 200, an inflation tube 104, and an inflation port 106. FIG. 2 is a closer view of the balloon assembly 200. The balloon assembly 200 includes the balloon 202 fixed to an inner body 204. In an alternate example, the inner body 204 can be formed integrally to the balloon 202. The inner body extends along an axis 208 from a proximal end 210 to a distal end 212 and includes a slit 206 used to mount the balloon assist device 100 to a catheter. Thus, the inner body 204 partially encloses the axis 208. FIGS. 3 and 4 illustrate one embodiment of attaching the balloon 202 to the inner body 204. In this embodiment, the balloon 202 includes a sheath 214 of flexible material which is joined to the inner body 204 around the perimeter 216 of the sheath 214. The sheath 214 may be made of an appropriate elastic or inelastic material, including polyimide. The volume enclosed between the sheath 214 and inner body 204 becomes the balloon 202.

FIG. 3 illustrates the balloon 202 in the deflated state. FIG. 4 illustrates the balloon 202 in the inflated state. Although a particular shape of the balloon 202 is illustrated, the disclosure is not limited to the shape shown. The balloon 202 is inflated using the inflation tube 104. Sterile water, saline or another appropriate solution may be introduced to the inflation tube 104 at the inflation port 106. The inflation port 106 may be one of several types known in the industry. In another embodiment, the balloon 202 and the inner body 204 are formed integrally with one another.

The slit 206 is provided along a length L of, and in certain examples, entirely through the length of the inner body 204 to permit the balloon assist device to mount to the exterior of a catheter 240. The catheter 240 can be as small as 6-8 F, which enhances ability of the invention to access distal vasculature. To mount the balloon assist device 100 on the catheter 240, the slit 206 is spread open and the catheter 240 is passed through the slit. The slit 206 is then reclosed. In one embodiment, the inner body 204 is made of a resilient material such as spring-temper stainless steel or, more preferably a superelastic material such as Nitinol. In such an embodiment, the slit 206 in the inner body 204 will reclose on its own due to the resilient nature of the inner body 204. In another embodiment the inner body 204 is formed integrally with the balloon 202.

Figure 5:
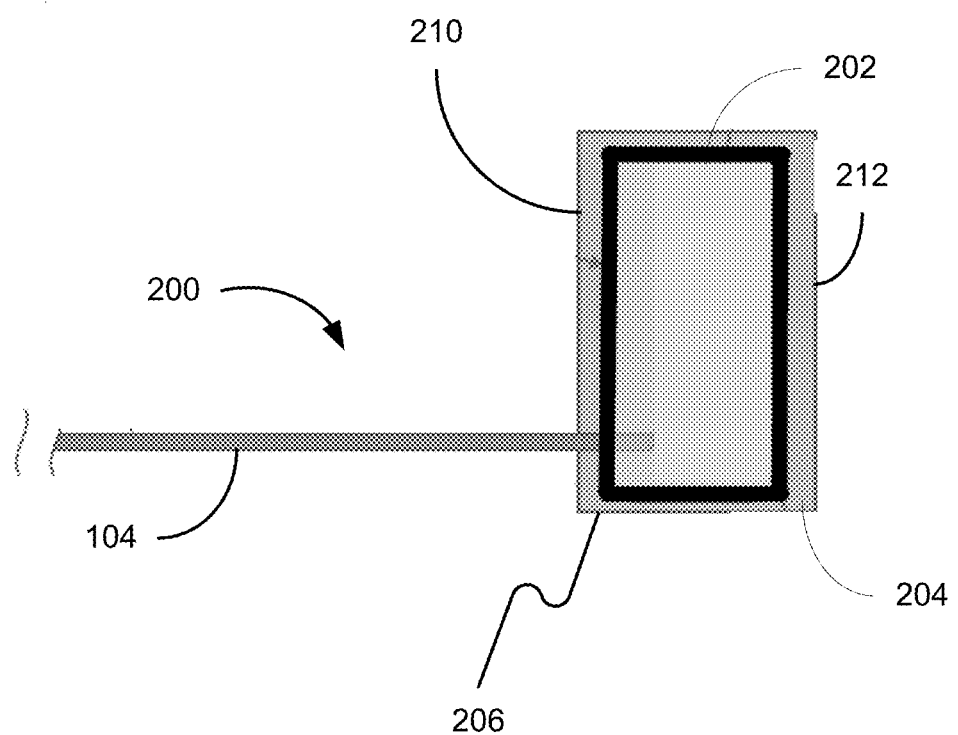
FIG. 5 is a diagram of the balloon assembly of the balloon assist device illustrating the balloon and inner body in a flattened state, in accordance with the present disclosure.

FIG. 5 illustrates one example where the balloon assembly 200 is first assembled in a flat configuration, where the shape of the inner body 204 and the sheath 214 can be more easily cut. The flat configuration also allows easier sealing of the sheath 214 to the inner body 204 around the sheath's perimeter 216. The sheath 214 may be sealed to the inner body 204 using a variety of techniques well-known in the industry including, without limitation, adhesives, thermal bonding, and radio-frequency (RF) bonding. In addition to the seal between the sheath 214 and in the inner body 204, the inflation tube 104 is in sealed communication with the inner volume of the balloon 202. The inflation tube 104 may be made from metal to facilitate pushability of the balloon 202 along the catheter 240, a polymeric material such as a polyimide for flexibility, or a combination of metal at the proximal end 210 and transitioning to the polymeric material as it extends toward the distal end 212. In some examples the inflation tube 104 may be used to advance the balloon assist device 100 along the catheter 240 in the distal direction and to retract it in the proximal direction. In other embodiments a separate pusher (not shown) may be attached to the inner body 204 to advance the balloon assist device 100 along the catheter 240 in the distal direction and to retract it in the proximal direction, allowing the inflation tube to be more flexible.

After sealing the sheath 214 to the inner body 204, the flat balloon assembly 200 can be formed into an appropriate shape for mounting to the catheter 240. In certain examples, the balloon assist device 100 can be manufactured/shipped in the flat orientation and bent around the catheter by a clinician. The final shape of the inner body 204 partially encloses the catheter 240 securely enough to track along catheter body inside the patient's vasculature during a procedure. In the embodiment shown the inner body 204 has a cylindrical shape, but other cross-sections may be used as needed.

Figure 6:
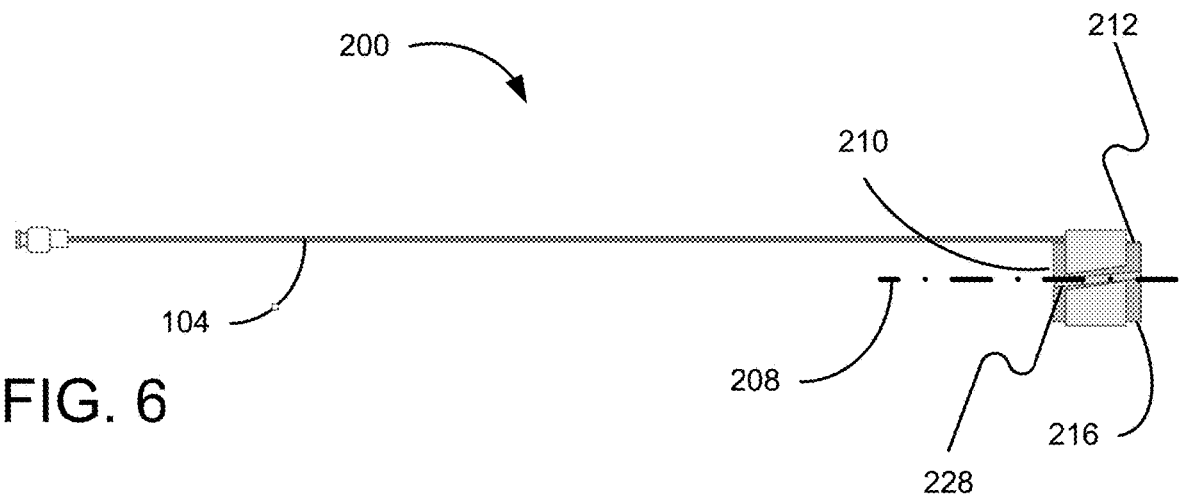
FIG. 6 is a diagram of an alternate embodiment of the balloon assist device where the inner body has a helical slit, in accordance with the present disclosure.
Figure 7:
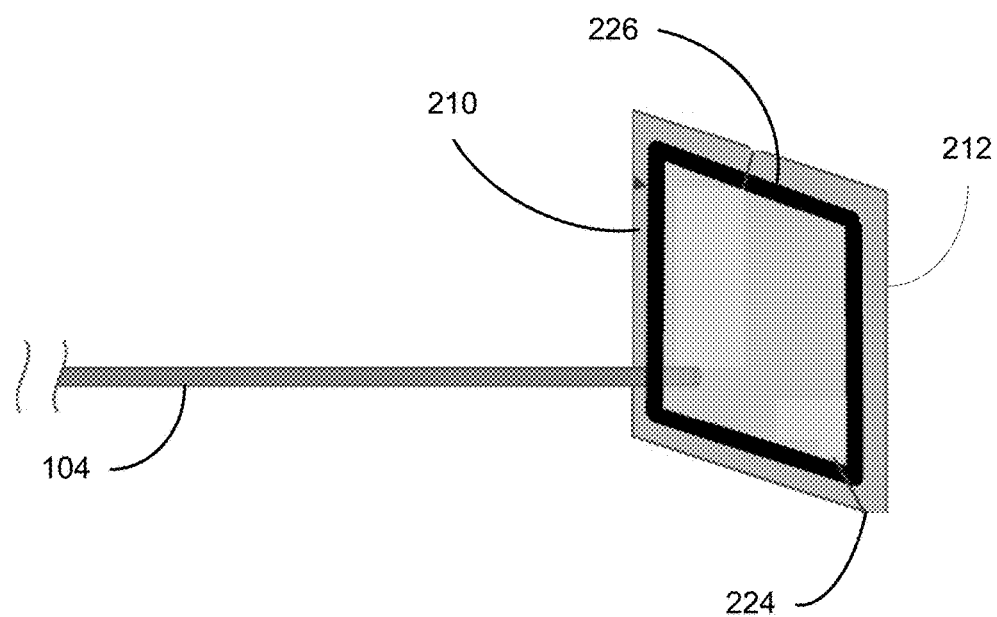
FIG. 7 is a diagram of an alternate embodiment of the balloon assembly of the balloon assist device illustrating the balloon and inner body in a flattened state, where the inner body has a helical slit, in accordance with the present disclosure.

In the embodiment shown in FIG. 5, the slit 206 in the inner body 204 is straight. That is, the slit 206 is parallel to the axis 208 and to the catheter 240. An alternative embodiment with a helical slit 228 is shown in FIG. 6. In this embodiment, the helical slit 228 coils around the axis 208 and the catheter 240 at least a quarter turn. A pre-formed flat version of this embodiment is shown in FIG. 7 as a non-limiting example to form the helical slit 228. Instead of rectangles, the inner body 224 and sheath 226 are cut into trapezoids (not illustrated). When these are formed into a cylinder they result in the helical slit 228.

Figure 8:
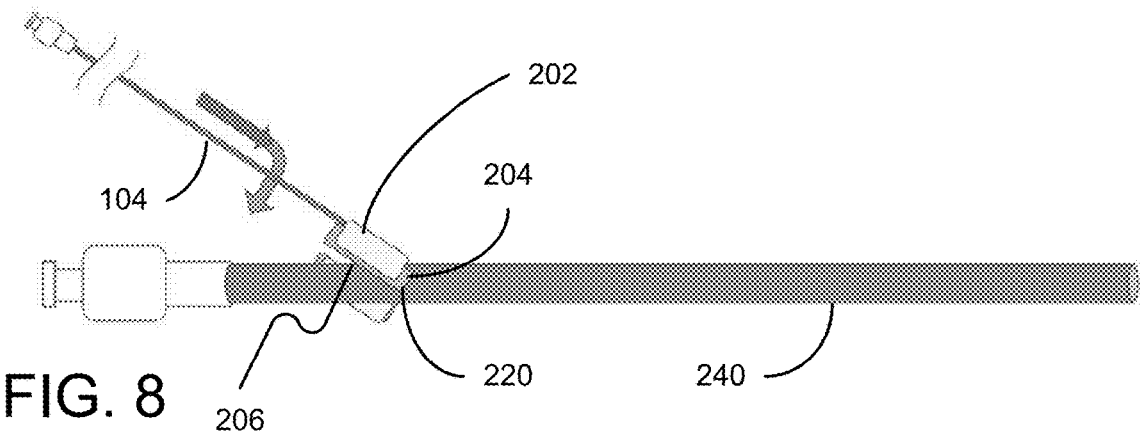
FIG. 8 is a diagram of the balloon assist device being mounted to the proximal end of the catheter body, in accordance with the present disclosure.
Figure 9:
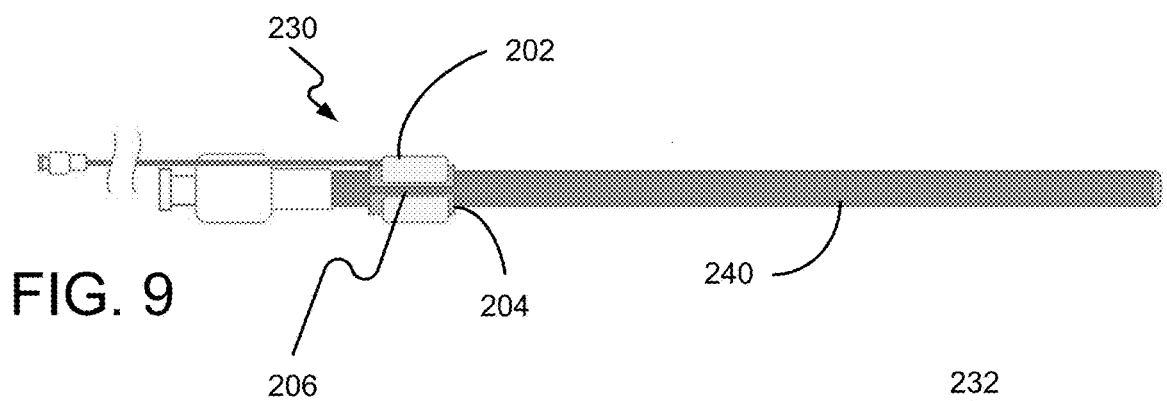
FIG. 9 is a diagram of the balloon assist device mounted on the proximal end of the catheter body, in accordance with the present disclosure.
Figure 10:
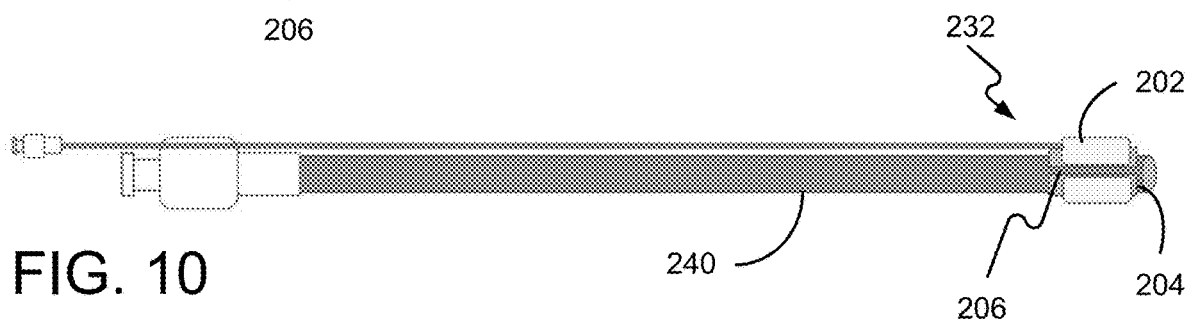
FIG. 10 is a diagram of the balloon assist device mounted on the catheter body and positioned at the distal end of the catheter, in accordance with the present disclosure.
Figure 11:
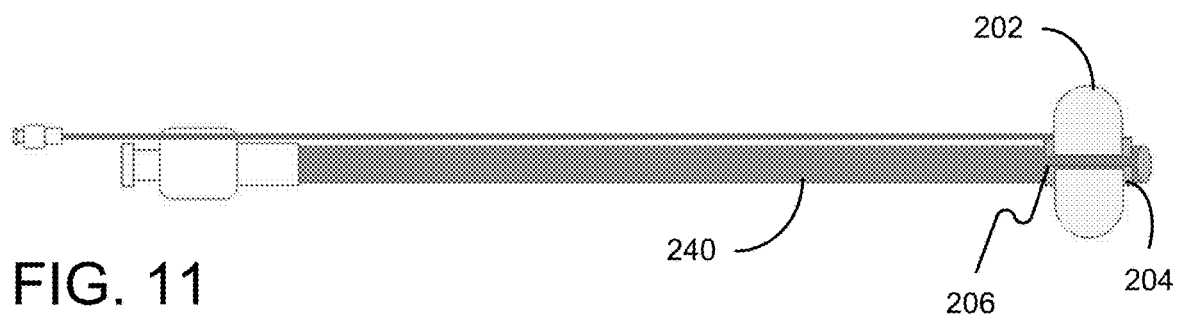
FIG. 11 is a diagram of the balloon assist device balloon inflated at the distal end of the catheter in accordance with the present disclosure.

FIGS. 8-11 show the basic operation of the balloon assist device 100. In FIG. 9 the balloon assist device 100 is mounted on the catheter 240. As explained above, the slit 206 is spread wide enough to accept the catheter 240. To ease the process, a corner 220 of the slit 206 may be initially spread to accept the catheter 240 and the process completed by twisting the balloon assist device 100 the rest of the way onto the catheter 240, as shown in FIG. 8. FIG. 9 shows the balloon assist device 100 fully mounted on the catheter 240 in a proximal position 230. The balloon assist device 100 is then slid along the catheter 240 using the inflation tube 104 or a separate pusher (not illustrated). FIG. 10 shows the balloon assist 100 mounted on the catheter 240 in the distal position 232 after sliding along the catheter 240. The balloon 202 is then inflated using the inflation tube 104, as shown in FIG. 11.

Figure 12:
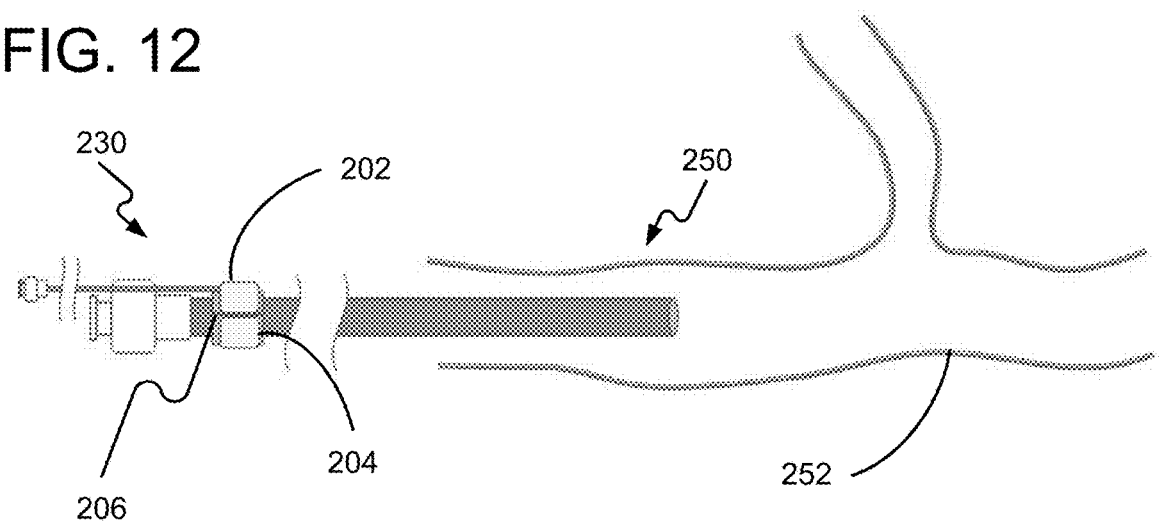
FIG. 12 is a diagram of a catheter positioned in a patient's vasculature with the balloon assist device mounted to the proximal end of the catheter body, in accordance with the present disclosure.
Figure 13:
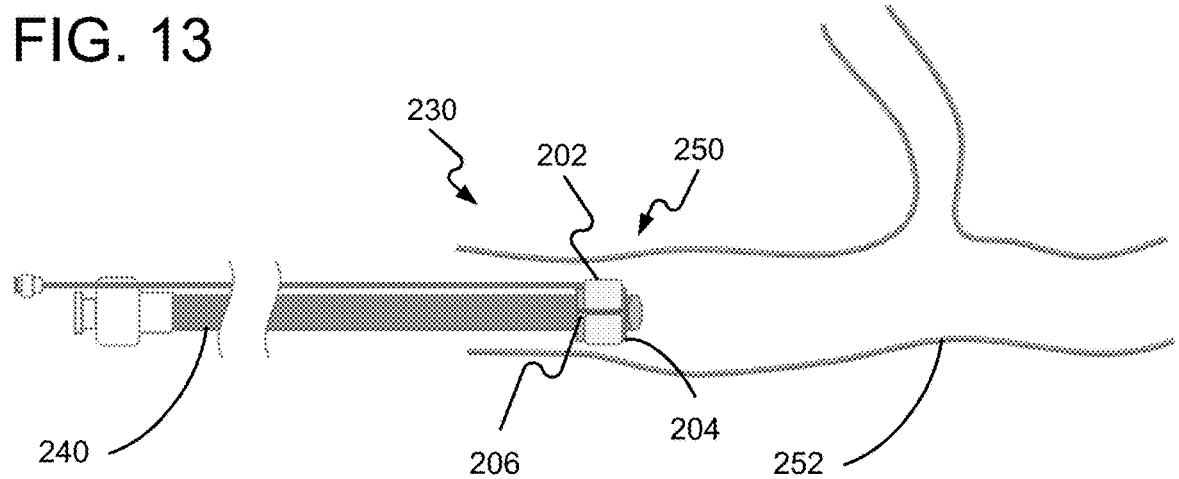
FIG. 13 is a diagram of a catheter positioned in a patient's vasculature with the balloon assist device positioned on the distal end of the catheter body at the treatment site, in accordance with the present disclosure.
Figure 14:
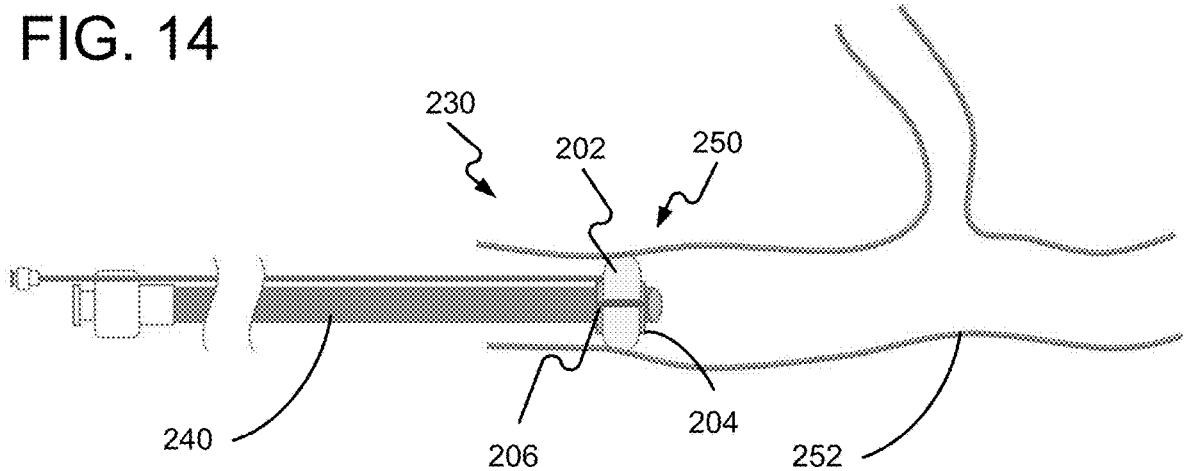
FIG. 14 is a diagram of a catheter positioned in a patient's vasculature with the balloon inflated at the treatment site, occluding a blood vessel, in accordance with the present disclosure.

FIGS. 12-14 show the basic operation of the balloon assist device 100 during a medical procedure. FIG. 12 shows the balloon assist device 100 fully mounted in the proximal position 230 on a catheter 240 which a clinician has already positioned at a treatment site 250 within a patient's vasculature 252. The balloon assist device 100 is then slid along the catheter 240 using the inflation tube 104 or a separate pusher (not illustrated) to treatment site 250. FIG. 10 shows the balloon assist device 100 mounted on the catheter 240 in the distal position 232 at the treatment site 250. The balloon 202 is then inflated using the inflation tube 104 to occlude part of the patient's vasculature 252, as shown in FIG. 11.

Figure 15:
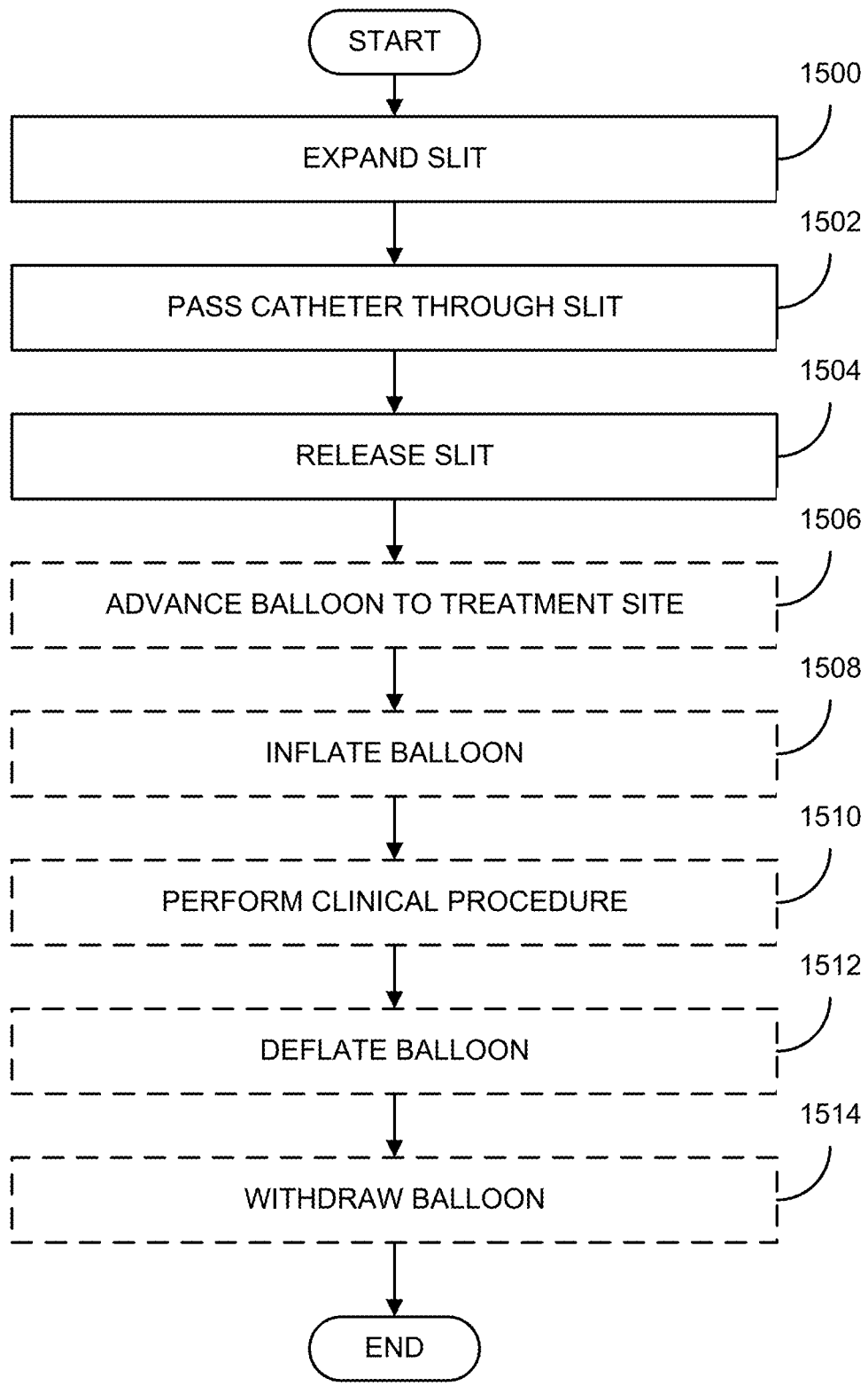
FIG. 15 is a flow chart illustrating one embodiment of a method for using the balloon assist device, in accordance with the present disclosure.

FIG. 15 is flow chart showing the steps for using the balloon assist device 100. At 1500 the slit 206 is expanded. At 1502 the catheter 240 is inserted through the expanded slit 206. At 1504 the expanded slit 206 is released to contract around the catheter 240, securely and slidably mounting the balloon assist device 100 to the catheter 240. The remaining steps are optional based on the clinical procedure. At 1506 a pusher is used to slide the balloon assist device 100 along the catheter 240 to a treatment site 250 in a patient's vasculature 252. In some embodiments the pusher may be the inflation tube 104. At 1508 the balloon assist device 100 is inflated at the treatment site 250 using the inflation tube 104. Alternately, at 1510 a procedure is performed while the inflated balloon assist device 100 occludes a blood vessel at the treatment site 250. At 1512 the balloon assist device 100 is deflated. At 1514 the deflated balloon assist device 100 is withdrawn.

To facilitate an understanding of the principals and features of the disclosed technology, illustrative embodiments are explained below. The components described hereinafter as making up various elements of the disclosed technology are intended to be illustrative and not restrictive. Many suitable components that would perform the same or similar functions as components described herein are intended to be embraced within the scope of the disclosed devices and methods. Such other components not described herein may include, but are not limited to, for example, components developed after development of the disclosed technology.

It must also be noted that, as used in the specification and the appended claims, the singular forms "a," "an" and "the" include plural referents unless the context clearly dictates otherwise.

By "comprising" or "containing" or "including" is meant that at least the named component or method step is present in the article or method, but does not exclude the presence of other components or method steps, even if the other such components or method steps have the same function as what is named.

It is also to be understood that the mention of one or more method steps does not preclude the presence of additional method steps or intervening method steps between those steps expressly identified. Similarly, it is also to be understood that the mention of one or more components in a device or system does not preclude the presence of additional components or intervening components between those components expressly identified.

The design and functionality described in this application is intended to be exemplary in nature and is not intended to limit the instant disclosure in any way. Those having ordinary skill in the art will appreciate that the teachings of the disclosure may be implemented in a variety of suitable forms, including those forms disclosed herein and additional forms known to those having ordinary skill in the art.

Certain embodiments of this technology are described above with reference to flow diagrams. Some blocks of the block diagrams and flow diagrams may not necessarily need to be performed in the order presented, or may not necessarily need to be performed at all, according to some embodiments of the disclosure.

While certain embodiments of this disclosure have been described in connection with what is presently considered to be the most practical and various embodiments, it is to be understood that this disclosure is not to be limited to the disclosed embodiments, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain embodiments of the technology and also to enable any person skilled in the art to practice certain embodiments of this technology, including making and using any apparatuses or systems and performing any incorporated methods. The patentable scope of certain embodiments of the technology is defined in the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

The invention claimed is:

1. A balloon assist device comprising:
    an inner body comprising resilient material and extending along an axis from a proximal end to a distal end and comprising a split cylinder comprising a cross-section divided by a slit radially offset from the axis of the inner body and in sealed communication with a balloon which partially encloses the axis, the inner body and the balloon configured to be expanded then releasably contract around an outer surface of a catheter;
    the balloon joined to the inner body and comprising an axial length shorter than an axial length of the inner body; and
    an inflation tube radially offset from the axis of the inner body and in sealed communication with the balloon.

2. The balloon assist device of claim 1 where the balloon comprises a sheath of flexible material separate from and bonded to the inner body and a volume between the sheath and the inner body which comprises the interior of the balloon.

3. The balloon assist device of claim 1 wherein once the inner body and the balloon are attached onto the outer surface of the catheter, the inner body and the balloon are both advanceable along the outer surface of the catheter from a proximal position of the catheter to a distal position of the catheter.

4. The balloon assist device of claim 1 wherein the split cylinder comprises a straight slit parallel to the axis from the proximal end to the distal end.

5. The balloon assist device of claim 1 wherein the split cylinder comprises a helical slit extending helically about the axis from the proximal end to the distal end.

6. The balloon assist device of claim 2 wherein the sheath is bonded to inner body along a perimeter having four sides which follow contours of an outer face of the split cylinder.

7. The balloon assist device of claim 6 wherein the sheath comprises an elastic material.

8. A balloon assisted catheter system comprising:
a catheter;
a balloon assist device, removably engaging an outside of the catheter, comprising:
an inner body comprising a split cylinder having a proximal and a distal end, the split cylinder comprising a cross-section divided by a slit radially offset from an axis of the inner body and partially encloses the axis between the proximal and distal ends, the inner body configured to be expanded then releasably contract around the outside of the catheter;
an inflatable balloon bonded to the inner body, the inflatable balloon comprising an axial length shorter than an axial length of the inner body; and
an inflation tube radially offset from the axis of the inner body and in sealed communication with the balloon.

9. The balloon assisted catheter system of claim 8 wherein the slit is a straight opening extending from the proximal end to the distal end.

10. The balloon assisted catheter system of claim 8 wherein the inflation tube is in sealed communication with an inflatable sheath separate from and bonded to the inner body.

11. The balloon assisted catheter system of claim 8 wherein once the inner body and the balloon are attached onto the outside of the catheter, the inner body and the balloon are both advanceable along the outside of the catheter from a proximal position of the catheter to a distal position of the catheter.

12. The balloon assisted catheter system of claim 8 wherein edges of the inflatable balloon are offset from edges of the inner body.

* * * * *